United States Patent
Wei (12)

(10) Patent No.: US 6,893,626 B2
(45) Date of Patent: May 17, 2005

(54) COMPOSITIONS FOR TRP-M8 BINDING AND RADIORECEPTOR METHODS THEREWITH

(76) Inventor: Edward T. Wei, 480 Grizzly Peak Blvd., Berkeley, CA (US) 94708

( * ) Notice: Subject to any disclaimer, the term of this patent is extended or adjusted under 35 U.S.C. 154(b) by 152 days.

(21) Appl. No.: 10/370,483

(22) Filed: Feb. 18, 2003

(65) Prior Publication Data

US 2004/0161751 A1 Aug. 19, 2004

(51) Int. Cl.$^7$ .............................................. A61K 51/00
(52) U.S. Cl. ........................................ 424/1.81; 568/14
(58) Field of Search .............................. 424/1.65, 1.81; 568/14

(56) References Cited

U.S. PATENT DOCUMENTS

| | | |
|---|---|---|
| 4,020,153 A | 4/1977 | Rowsell et al. |
| 4,034,109 A | 7/1977 | Rowsell et al. |
| 4,070,449 A | 1/1978 | Rowsell et al. |
| 4,070,496 A | 1/1978 | Rowsell et al. |
| 5,976,492 A | 11/1999 | Griffiths et al. |
| 6,194,152 B1 | 2/2001 | Laus et al. |

OTHER PUBLICATIONS

CA:131:197592 abs of Journal of Labelled Compounds and Radiopharm. by Fortineau et al 42(6) pp 527–536 1999.*
Chemical abstracts vol. 59 No. 14812(b) 1963.*
CA:100:153343 abs of Analytical Biochemistry by Savabi et al 137(2) pp 374–9 1984.*
CA:115:115014 abs of CS 267547 Feb. 1990.*
CA:102:132161 abs of Radiokhimiya by Makarov et al 26(6) pp 818–22 1984.*
Tsavaler, et al., Cancer Research 61: 3760–3769; May 1, 2001; "Trp–p8, a novel prostate–specific gene . . . ".
Zhang and Casida, J. Organic Chemistry 66: 327–329; Dec. 2, 2000.

* cited by examiner

Primary Examiner—Jean F. Vollano

(57) ABSTRACT

One embodiment of the invention is a composition that comprises a radioactive $^{32}$P or $^{33}$P phosphine oxide molecule. The said composition is designed to bind to the transient potential receptor-M8 (TRP-M8) receptor of cells. The radioactive $^{32}$P or $^{33}$P phosphine oxide ligand may be used for radioreceptor binding studies and for diagnostic studies of cancerous tissues. The TRP-M8 receptor is selectively expressed in malignant tissues such as prostate cancer cells. Affinity of the $^{32}$P or $^{33}$P phosphine oxide ligand for the TRP-M8 receptor confers selectively and specificity in delivering lethal radiation to the diseased cells.

7 Claims, No Drawings

COMPOSITIONS FOR TRP-M8 BINDING AND RADIORECEPTOR METHODS THEREWITH

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

This invention generally relates to chemicals that bind to receptors in the TRP (transient receptor potential) ion channel family, more particularly to the subgroup of long TRP (or TRPM) channels, and most particularly to those that specifically bind to the TRP channel called "trp-p-8" (or TRP-M8); TRP-M8 receptors being present at elevated levels in certain cancers, such as prostate cancer. This invention more particularly relates to compositions containing radioactive phosphorus ($^{32}$P or $^{33}$P) within the molecular structure, said compositions which are useful, for example, in radioreceptor applications.

2. Description of Related Art

Laus et al. (Prostate tumor polynucleotide compositions and methods of detection thereof) in U.S. Pat. No. 6,194,152, issued Feb. 27, 2001, herein incorporated by reference, described a novel polynucleotide and the polypeptide encoded by it, that was detected exclusively in human prostate tumor cells, but not in non-malignant tissues such as the brain, visceral organs, or glands. The mRNA for the synthesis of this specific protein was also detected in samples of malignant mammary gland, melanoma, and colorectal cancer cells. The 1044 amino acid protein, deciphered from the cDNA sequence, was named trp-p-8 because of its structural homology to receptors of the transient receptor potential (TRP) family. A paper describing this gene/protein was published in Cancer Research (vol. 61 pg. 3760–3769, May 1, 2001. L. Tsavaler, M. H. Shapero, S. Morkowski, and R. Laus: "Trp-p8, a novel prostate-specific gene, is up-regulated in prostate cancer and other malignancies and shares high homology with transient receptor potential calcium channel proteins.")

The trp-p-8 is preferably named TRP-M8 because of its structural homology to other protein receptors in this family. The identifying tags for the sequences in the NicePro TrEMBL Database are Q8R405 (mouse TRP-M8) Q8R444 (rat TRP-M8 or CMR1) and Q8TAC3 (human TRP-M8, or trp-p-8).

Prostate cancer is the most common cancer among men in the United States. Despite the fact that this cancer was diagnosed in almost 200,000 U.S. men in the year 2002 (and will lead to the death of over 30,000 men), there is no universally agreed-upon strategic plan for its diagnosis and management. Brachytherapy, a treatment well known in the art, involves the implantation of radioactive seeds directly into the prostate gland. The radioactive seeds used in brachytherapy may include iodine-131, palladium, radium, iridium, cesium, or phosphorus.

In the past, various radioactive phosphorus compounds have been used clinically in some oncological applications, for example for the treatment of ovarian cancer, leukemia, and for treating polycythemia rubra vera (uncontrolled proliferation of red blood cells). Their use, however, suffers from the inability to precisely target the malignant cells, which subjects the patient to potentially severe toxic side effects. More specific radioisotopes are needed that directly target malignant tissue and cells to improve diagnosis and treatment of certain cancers. Such radioisotopes are disclosed herein.

BRIEF SUMMARY OF THE INVENTION

In one aspect of the present invention, compositions having $^{32}$P- or $^{33}$P-containing phosphine oxide molecules with specific affinity for the TRP-M8 receptor are provided. These compositions are useful for laboratory tests, called radioreceptor assays, and potentially useful for radiotherapy. More particularly, the invention relates to trialkyl and dialkylcycloalkyl $^{32}$P- and $^{33}$P-phosphine oxide molecules that selectively bind to TRP-M8 sites in hyperplastic and cancerous cells and tissues.

Among preferred embodiment compositions are those comprising a radioactive compound having the structure $R_1$ $R_2$ $R_3$ [*P]=O, wherein *P is $^{32}$P or $^{33}$P, $R_1$ is a straight chain alkyl of from 4–8 carbons, $R_2$ is a branched carbon chain of from 3–5 carbons, $R_3$ is an alkyl group of 3–6 carbons or a cyclopentyl group, and $R_1$, $R_2$, and $R_3$ together have from 13–16 carbons. Each radioactive compound of the present invention has a specific activity of at least about 20 Ci/mmol, more preferably has a specific activity of at least about 250 Ci/mmol. Each radioactive compounds is a ligand for the TRP-M8 receptor, and preferably each has a Kd for the receptor of about $1\times10^{-12}$ to $1\times10^{-5}$ molar.

A novel and unique aspect of the present invention is that $^{32}$P and $^{33}$P radionuclides are incorporated (i.e. covalently bound) within the molecular agonist structure of the ligand for the receptor. One advantage of this is that the radiation emitted from $^{32}$P and $^{33}$P, which can readily be detected with radioactivity counters, is directly correlated to high affinity binding to TRP-M8 receptors. Such specific direct radioactive label incorporation into the binding molecule is uncommon, exceptional, and provides excellent results in radioreceptor applications as contemplated in the present invention. By contrast, a laboratory procedure, for example, the labeling of a binding protein such as a monoclonal antibody by $^{125}$I or $^{131}$I, carries the risk that the protein will be denatured by the iodine, thereby reducing or destroying its high affinity binding to the receptor target. Moreover, the points of attachment of iodine to the binding molecule are non-specific (see Griffiths et al. Radioactive phosphorus labeled proteins for targeted radiotherapy. U.S. Pat. No. 5,976,492, issued Nov. 2, 1999, herein incorporated by reference).

Incorporating $^{32}$P and $^{33}$P into the molecules of the present invention avoids the drawbacks referred to above with radioactive iodine with respect to denaturation and potential loss of activity, since incorporation of the radio-isotope into the molecule does not change the physical-chemical properties of the molecule. The chemical features of the molecule that determine specificity of binding affinity are retained, and added to it is the property of beta radiation.

Particularly preferred compositions of the present invention comprise diisobutyl-n-heptylphosphine($^{32}$P or $^{33}$P) oxide and iso-butyl-sec-butyl n-heptyl phosphine($^{32}$P or $^{33}$P) oxide, as exemplary examples of trialkyl ($^{32}$P or $^{33}$P) phosphine oxide compounds having high affinity for the TRP-M8 receptor.

DETAILED DESCRIPTION OF THE INVENTION

Chemistry of Phosphine Oxide Ligands for the TRP-M8 Receptor

The compounds having the desired affinity for the TRP-M8 receptor and contemplated for use in the present invention also include those with $^{35}$S in their structure, as will be discussed infra, but more preferably are $^{32}$P or $^{33}$P phosphine oxides illustrated by Formula 1:

$$R_1R_2R_3[*P]=O \qquad \text{Formula 1}$$

In Formula 1, wherein, *P is $^{32}$P or $^{33}$P; and $R_1$ is an alkyl radical containing at least 3 carbon atoms, $R_2$ is an alkyl radical containing at least 3 carbon atoms or a cycloalkyl radical and $R_3$ is an alkyl or cycloalkyl radical, $R_1$, $R_2$ and $R_3$ together present a total of from 13–17 carbon atoms, and At least one of $R_1$, $R_2$ and $R_3$ has branching in an α, β or γ position relative to the $^{32}$P or $^{33}$P (phosphorus) atom. Branching in this context is to be taken to include cyclic structures, as well as branched chain acyclic groups. Preferably $R_1$, $R_2$ and $R_3$ are such that any two, when taken together, present a total of at least 6 carbon atoms.

Compounds of highest activity and especially preferred for use in the present invention are those wherein $R_1$ is a straight chain alkyl group of from 4–8 carbon atoms, more especially 5–8 carbon atoms, wherein $R_2$ is a branched chain alkyl group of from 3–5 carbon atoms, ($R_2$ especially being an isopropyl, secondary-butyl, isobutyl or an isopentyl group); and wherein $R_3$ is an alkyl group, preferably a branched chain alkyl group, of from 3–6 carbon atoms, preferably 4 or 5 carbon atoms, or a cyclopentyl group, and $R_1$, $R_2$ and $R_3$ providing a total of from 13–16 carbon atoms (see Table 1, infra).

The naturally occurring isotope of phosphorus is $^{31}$P with an atomic mass of 30.97 Daltons. The radioactive isotopes of phosphorus are $^{32}$P and $^{33}$P both of which decay by β (electron) emission (i.e. "beta radiation") to the respective sulfur atom with half-lives of 14.28 days and 25.3 days, respectively. $^{32}$P releases beta radiation of 1.71 Mev (maximal energy) and $^{33}$P releases beta radiation of 0.249 Mev (maximal energy). $^{32}$P and $^{33}$P are inexpensive, readily available in high specific activity and have therapeutically desirable half-lives. These radioactive isotopes emit only beta-radiation and have an excellent depth penetration in tissue of approximately 6 mm. Phosphorus, being a common constituent of the body, has no inherent toxicity in its radioactive form, other than the emitted radiation.

TABLE 1

Phosphine Oxide Compounds
(Basic Structure: $R_1$, $R_2$, $R_3$ ($^{32}$P=O or $^{33}$P=O))

| $R_1$ | $R_2$ | $R_3$ |
|---|---|---|
| n-$C_7H_{15}$ | iso-$C_4H_9$ | sec-$C_4H_9$ |
| n-$C_7H_{15}$ | iso-$C_3H_7$ | sec-$C_4H_9$ |
| n-$C_8H_{17}$ | iso-$C_3H_7$ | sec-$C_4H_9$ |
| n-$C_8H_{17}$ | iso-$C_4H_9$ | sec-$C_4H_9$ |
| n-$C_6H_{13}$ | iso-$C_4H_9$ | sec-$C_4H_9$ |
| n-$C_8H_{17}$ | sec-$C_4H_9$ | sec-$C_4H_9$ |
| n-$C_6H_{13}$ | iso-$C_3H_7$ | sec-$C_4H_9$ |
| n-$C_6H_{13}$ | iso-$C_3H_7$ | cyclo-$C_5H_9$ |

Conventional Phosphine Oxide Preparation

Conventional preparations of phosphine oxides (without using the radioactive precursor), using protocols well known in the art, are disclosed by Rowsell and Spring in U.S. Pat. No. 4,070,496, issued Jan. 24, 1978, herein incorporated by reference. If two alkyl groups are the same, then dialkylphosphinyl chlorides, $R_1R_1$ POCl, may be prepared by the action of Grignard reagents on phosphite, after chlorination. These dialkyl phosphinyl chlorides will then further react with another specified Grignard reagent to form the desired tertiary phosphine oxides. If all three alkyl groups of a tertiary phosphine oxide are different, then the alternative reaction between a Grignard reagent, RMGX, and chlorophosphite gives dialkyl phosphinite. This latter compound, when allowed to react with a Grignard reagent, R'MgX, will give the unsymmetrical secondary phosphine oxide, RR'(P)(O)H. Tertiary phosphine oxides can be prepared from these secondary phosphine oxides. Some of these standard reactions (with non-radioactive P) are described in Organic Phosphorus Compounds, Volumes 3 and 4, edited by G. M. Kosolapoff and L. Maier, published by Wiley-Interscience, 1972. The general principals for the reaction of Grignard reagents with halides and esters of phosphorous acids are well-known to practitioners of the art (G. M. Kosolapoff. Organophosphorus Compounds, New York, Wiley, pg. 107 to 109, 1950).

For example, in the preparation of non-radioactive diisobutyl-n-heptylphosphine oxide (Methods for preparing diisobutylphosphinyl chloride by chlorinating diisobutylphosphine oxide, described by R. H. Williams, L. A. Hamilton J. Am. Chem. Soc. (1952), 74, 5418), a solution of diisobutylphosphinyl chloride (3.9 gm) in tetrahydrofuran (50 ml.) was added dropwise to a refluxing solution of n-heptylmagnesium bromide (prepared from magnesium turnings (1.2 gm), n-heptyl bromide (9.0 gm) and tetrahydrofuran (100 ml.)). The mixture was heated under reflux for 18 hours. After cooling to room temperature, the reaction mixture was poured onto ice and 2N HCl (300 ml.), and extracted with methylene dichloride. The combined extracts were washed with lithium hypochlorite solution, 2N NaOH solution and finally with water, then dried (MgSO$_4$). The solvent was removed by distillation and the residual yellow oil (8 gm) was eluted with chloroform down a silica gel column. The product ($R_f$=0.1 to 0.2 on silica t.l.c. (CHCl$_3$)) was finally distilled to yield diisobutyl-n-heptyl-phosphine oxide (coded as WS148) as a colorless liquid, bp. 120° C.

Synthesis of Radioactive Ligands for the Trp-M8 Receptor.

Amersham Biosciences Corporation (800 Centennial Avenue, Piscataway, N.J. 08855-1327, USA) is a major supplier of reagents for the synthesis of radio-labeled chemicals. Starting materials for $^{32}$P and $^{33}$P compounds can be obtained from Amersham at the specific activities listed Table 2 below. Starting compounds for $^{35}$S compounds can also be obtained from Amersham.

TABLE 2

| Radionuclide | Maximum Specific Activity | Typical Specific Activity for Labeled Compounds |
|---|---|---|
| Phosphorus-32 | 9130 Ci/matom | 1 to 6000 Ci/mmol |
| Phosphorus-33 | 5120 Ci/matom | 2500 Ci/mmol |
| Sulfur-35 | 1490 Ci/matom | 1 mCi to 1000 Ci/mmol |

The radiosynthesis of trialkyl-, dialkylcycloalkyl-[$^{32}$P] or [$^{33}$P]-labeled phosphine oxide described in this invention begins with the formation of the phosphorus-carbon bond starting from the most readily available precursors, [$^{32}$P]-phosphoric acid (H$_3$PO$_4$) or [$^{33}$P]-phosphoric acid.

Zhang and Casida, (Novel synthesis of [$^{33}$P]-(2-chlorethyl)-phosphonic acid, J. Organic Chemistry 66:

327–329, 2001), described an excellent method for reducing [*P]-phosphoric acid to [*P]-PCl$_3$, [*P]-POCl$_3$, and [*P]-phosphorous acid. These reduced products then react with other entities to form the phosphorus-carbon bond. Starting with an aqueous solution of [$^{33}$P]-H$_3$—PO$_4$, 2 mCi weighing about 10 nanograms in 1 ml of water, treatment with phosphorus pentachloride (PCl$_5$), resulted in conversion not only of H$_2$O (the solvent) to POCl$_3$ but also of [$^{33}$P]-H$_3$PO$_4$ to [$^{33}$P]-POCl$_3$. Reaction with PPh$_3$ (triphenylphosphine) in toluene under reflux condition reduced [$^{33}$P]-POCl$_3$ to [$^{33}$P]-PCl$_3$ which was then hydrolyzed to [$^{33}$P]-H$_3$PO$_3$. Subsequent reaction of [$^{33}$P]-H$_3$PO$_3$ with BSTFA (N,O-bis (trimethylsilyl)trifluoroacetamide) afforded [$^{33}$P]-P(OTMS)$_3$ [tris(trimethylsilyl)phosphite]; using 1-bromo-2-chloroethane as the solvent, the reaction proceeded directly in situ to give phosphonate. Mild hydrolysis gave essentially pure [$^{33}$P]-2-chloroethyl-phosphonic acid in 70% overall chemical and radiochemical yields. The incorporation efficiency of radioactivity was nearly quantitative.

At different stages of this process, the various reduced products of [*P]-PCl$_3$, [*P]-POCl$_3$, and [*P]-phosphorous, may be removed and reacted with an alkyl halide or a Grignard reagent, using skills well-known in the art. The products of such reactions will generate the precursors as well as the final stable $^{32}$P and $^{33}$P dialkylcycoalkyl and trialkyl compounds with high affinity for the TRP-M8 receptors.

$^{35}$S-Containing Molecules $^{35}$S is a sulfur isotope with a half life of 87.4 days and beta radiation of 0.167 Mev. It can be obtained as the sulfate or elemental sulfur at a specific activity of up to 1000 Ci/mmole. The longer half-life of $^{35}$S, as compared to $^{32}$P or $^{33}$P, has certain advantages as a TRP-M8 ligand. For example, after 50 days, 67.3% of specific radioactivity is still present in the molecule containing a $^{35}$S radioisotope. The beta radiation energy emanating from $^{35}$S is, however, low and may not be sufficient to be lethal to hyperplastic and malignant cells, although this amount of radiation can still be readily detected in radioreceptor assays employed in diagnostic purposes. $^{35}$S-containing TRP-M8 agonists are contemplated to be somewhat less attractive candidates than $^{32}$P or $^{33}$P isotopes in practicing this invention.

The preferred $^{32}$P or $^{33}$P phosphine oxides contemplated in the present invention typically have a molecular weight in the range of 200 to 290 Daltons (13 to 17 carbon atoms, 25 to 35 hydrogen atoms, 1 oxygen atom, and 1 phosphorus atom). From these quantitative parameters, it can be readily seen that high specific activity $^{32}$P or $^{33}$P phosphine oxides may be synthesized. For example, a $^{32}$P or $^{33}$P phosphine oxide of 250 molecular weight, may be synthesized at a specific activity of 250 Ci/mmol to give a compound with a specific activity of one Ci/mg.

Use of $^{32\ or\ 33}$P Phosphine Oxide Radioligands for Receptor Assays

The TRP-M8 receptor is a functional, physiological receptor designed to detect temperature changes in its environment and to transmit this signal to the central nervous system so that appropriate regulatory responses can be initiated (e.g. vasoconstriction to reduce heat loss, putting on warmer clothing, avoiding the cold environment). This receptor also responds to chemicals including drug ligands (e.g., menthol and icilin), which activate its message transmission system. The functional role, if any, of TRP-M8 receptors on malignant prostate cells is not known. A receptor of this type has two integral components, an extracellular ligand binding domain that detects the ligand signal and an intracellular domain that is involved in signal transmission.

The ligand detection mechanism is structurally specific and analogous to the lock and key model of classical pharmacology. The key is the drug ligand and the lock is the receptor. Signal-transducing receptors are present in small numbers, on the order of a few thousand receptors per cell. Nevertheless, the receptors are designed to regulate crucial cellular functions and therefore become specific targets for drug discovery and development.

To measure drug occupancy of the receptor, pharmacologists use the term "Kd (dissociation constant)" to represent the affinity of the drug to its receptor. The Kd is based on the concentration of the drug occupying 50% of the receptor population, so the lower the Kd, the higher the "affinity" or stickiness of the ligand for its receptor. A drug receptor agonist, that is, a drug that elicits a biological response, generally has Kd values in the sub-micromolar ($10^{-6}$), nanomolar ($10^{-9}$) to picomolar ($10^{-12}$) concentration and represents a "high affinity" binding site. To measure Kd for different chemicals, it is necessary to have a primary radioligand, known to elicit the desired receptor response (for TRP-M8, it can be the sensation of cold, or cation influx into transfected cells that express the receptor), that is chemically pure and stable. The specific activity of the radioactive ligand must be high enough to detect high affinity binding of the receptor in the tissue being studied. This usually means a specific radioactivity of 30 Ci/mmol or higher.

A synthetic ($^{32}$P or $^{33}$P)phosphine oxide ligand, such as diisobutyl-n-heptylphosphine($^{32\ or\ 33}$P)oxide, is an excellent receptor-assay radioligand. A ($^{32\ or\ 33}$P) phosphine oxide radioligand, such as diisobutyl-n-heptylphosphine($^{32\ or\ 33}$P) oxide (code name WS148* wherein "*" means that the WS148 has a $^{32}$P or $^{33}$P in place of a $^{31}$P) can be synthesized, for example, at 30 Ci/mmole, which is considerably below the theoretical maximum of 6000 Ci/mmole for $^{32}$P. This ligand can then be used for radioreceptor assays of TRP-M8 agonists, as illustrated by Example 2. A TRP-M8 receptor assay based on ($^{32\ or\ 33}$P) phosphine oxide radioligands has several applications, as described infra.

Use of a ($^{32\ or\ 33}$P)-Phosphine Oxide Radioligand for Diagnostic Studies of Cancer and for Autoradiographic Studies in the Laboratory.

The TRP-M8 receptor is exceptional in that its mRNA transcript is found in abundance in biopsy samples of human malignant tissues such as breast cancer, colorectal cancer, melanoma and especially prostate cancer, but not in normal tissues with the exception of normal prostate epithelial cells (Tsavaler et al., supra). The standard method used for detecting TRP-M8 mRNA transcript in human tissues is to use in situ hybridization techniques with special riboprobes designed to detect the TRP-M8 cDNA. Serial sections of tissues are made, then stained, which enable histopathologists to visually observe any TRP-M8 receptors in the stained tissue. Such methods, however, require advanced laboratory skills and training. More recently, TRP-M8 antibodies have been developed that allow for the detection of TRP-M8 receptor protein on the surface of hyperplastic and malignant in prostate tissues. The use of said antibodies (that is "TRP-M8 immunocytochemistry") has confirmed the presence of TRP-M8 on the surface of human prostate cancer cells. A radioreceptor assay in accordance with the present invention, designed to measure the amount and the presence of the TRP-M8 receptor protein in biopsy samples, is potentially a less costly and a more convenient and direct alternative than the aforedescribed techniques of in situ hybridization and TRP-M8 immunocytochemistry.

The radioreceptor assay technique has diagnostic applications for patients having cancers that express the TRP-M8 receptor. For example, a biopsy sample of about 10 mg tissue may be homogenized and incubated with a ($^{32}$ or $^{33}$P)-phosphine oxide radioligand for 30 minutes, centrifuged or filtered, dissolved in a solvent and the beta-emissions counted on a Geiger, scintillation, or other radioactive counter. Based on the findings of Tsavaler et al, supra, one would expect a sharp increase in the density of TRP-M8 binding (Bmax) in malignant tissues, and the absence of any binding in normal tissues. Such measurements, with small amounts of tissue, because of the sensitivity of a radioreceptor method using a radioligand with high specific activity, can be used, for example, to detect the presence of diseased tissues, to track disease progression, and to measure metastases.

In the laboratory, $^{32}$P is widely used in a technique called the Southern blot. This technique is used in the detection and characterization of specific DNA sequences. $^{32}$P is incubated with DNA and the radiolabel visualized by autoradiography. By the same principles, the ($^{32}$ or $^{33}$)P-phosphine oxide radioligand may also be used in accordance with this invention for autoradiographic studies of the TRP-M8 receptor and for discerning its role in hyperplastic and neoplastic processes. For example, sections of prostate tissues may be incubated with the radioligand, rinsed, and then placed on X-ray film, and the precise sites of TRP-M8 localization mapped by autoradiography. The availability of the compositions of the present invention should facilitate the study of TRP-M8 expression in hyperplastic and malignant cells and aid in elucidating the role of TRP-M8 in tumor initiation, transformation, invasiveness and metastatic activity, perhaps even enabling scans of organs in vivo.

Bioassay of Activities of Phosphine Oxides on the TRP-M8 Receptor

An agonist in pharmacological terminology, is a chemical that activates biological events. The agonist, almost by definition, acts on a specific biological receptor to initiate cellular events. The purpose of a radioreceptor assay is to have methods to identify and measure ligands with low Kd value, and hence high affinity for the desired receptor. Thus, in practice, the first step is the characterization of a prototype ($^{32}$P or $^{33}$P)-phosphine oxide agonist of the TRP-M8 receptor. Once, a prototype has been identified, additional assays of in vitro and in vivo agonist activity are conducted to demonstrate that the binding is functional. These bioassays may also be conducted with non-radioactive phosphine oxides to measure the median effective dose (ED50). Also, especially if the phosphine oxide is to be administered in vivo, the chemical with the best therapeutic index, defined as the ratio of the Toxic Dose (TD50) divided by the Effective Dose (ED50), should be selected.

The Toxic Dose (TD) is an example of an ED in which the effect has adverse consequences. The TD can be measured by quantifying the median lethal dose (LD50) of a chemical in laboratory species such as the mouse and the rat. Additional tests of phosphine oxides on esterase enzymes, such as cholinesterase and neurotoxic esterases, can be conducted to rule out inhibition of enzymatic activity in such targets of nervous tissues. These bioassays will permit the selection of the most potent phosphine oxide analog for radiolabeling and further investigation. It should be noted, however, the radiotherapeutic dose (*ED of a $^{32}$P or $^{33}$P-phosphine oxide agonist of the TRP-M8 receptor) will be much less than the non-radioactive ED, hence a much greater margin of safety is obtainable.

Radiotherapeutic Use of $^{32}$P or $^{33}$P Phosphine Oxide Molecules with Affinity for the TRP-M8 Receptor.

The expression of TRP-M8 receptor in tissues of the prostate [see Laus et al., supra, and Tsavaler et al. supra for background information concerning TRP-M8 receptor expression in various cells and tissues], makes this receptor a potential target for treatment of benign prostatic hypertrophy. The expression of TRP-M8 receptor in malignant tissues of the prostate, mammary gland and colon [Laus et al., supra, and Tsavaler et al. supra], makes this receptor a potential target for cancer therapy. The drug designed for the target must be selective and specific: selective in the sense that hyperplastic or cancer cells express this target more than normal cells, and specific in the sense that the molecular target will have structural features that bind the drug with high affinity. Standard pharmacological strategies for targeting such a receptor expressed in tumors are to:

a) make a monoclonal antibody against TRP-M8. The binding of the monoclonal antibody to the receptor leads to cell death, for example, by triggering apoptosis;

b) target a small molecule agonist of TRP-M8 to the receptor to cause excess entry of calcium into cells bearing the TRP-M8 receptor. Calcium levels in cells are tightly regulated, and it may be possible to devise a small molecule to manipulate the TRP-M8 coupled calcium channels in such a manner as to cause cell death; and c) devise an epitope based on the TRP-M8 structure such that the body will develop an antibody response to TRP-M8. An immune system attack against TRP-M8-containing malignant cells may reduce cancer growth.

I wish to note a fourth alternative, an alternative that is novel, non-obvious, and more elegant. A ($^{32}$P or $^{33}$P)-phosphine oxide agonist of the TRP-M8 receptor with high affinity binding for this receptor may be a "magic bullet" for killing cancer cells bearing this receptor. Here, the binding affinity (that is, the address to the receptor) is an innate part of the molecular framework containing the radioactive phosphorus atom, and the beta radiation from $^{32}$P or $^{33}$P is the lethal message. Unlike the current brachytherapy technique, the molecules of the present invention will possess selectivity and specificity, in effect functioning as sophisticated letter-bombs with specific addresses for the target.

The high specific radioactivity that may be attained with a $^{32}$P or $^{33}$P radioisotope offers tremendous therapeutic advantage if the radiation can be focused on a localized target. Standard doses of intravenous sodium phosphate-$^{32}$P (0.13 mg/ml) for leukemia are 7 milliCi per 70 kg adult (1.73 square meters body surface). The dose for polycythemia vera is 2.9 milliCi. Similarly, a radiation dose of sodium iodide-$^{131}$I, for the treatment of thyroid malignancy, administered orally as a capsule, can range from 0.75 to 100 milliCi. As noted earlier, $^{32}$P phosphine oxide of 200–290 Daltons, may easily be synthesized at a specific activity of 250 Ci/mmol or higher to give a compound with a specific activity of greater than 1 Ci/mg. Injection or oral intake of 0.1 mg of such compounds will yield therapeutic dose of $\geq$100 milliCi. Because this radiation is believed to be selectively localized to hyperplastic or malignant cells, normal cells are spared and desirable therapeutic effects achieved.

To carry out such therapeutic applications, the following procedures are contemplated. The anti-tumor activity of a given ($^{32}$P or $^{33}$P)-phosphine oxide agonist of the TRP-M8 receptor may first be measured by its anti-proliferative actions (versus the non-radioactive isotope) on human tumor cell lines expressing the TRP-M8 receptor. If activity is found with EC50 ranges of between nanomolar to low micromolar concentrations, then the ($^{32}$P and $^{33}$P)-phosphine oxide agonist will be tested in nude mice bearing transplanted human tumor cell lines expressing the TRP-M8 receptor. Tumor volume, rate of growth, distant metastases, and histological features of the cancer cells in nude mice will be evaluated using standard techniques that are well known in the art. Pre-clinical in vivo test results from the nude mouse model and other animal models of cancer are the final prelude to clinical evaluation of the drug candidate in humans.

Before a ($^{32}$P or $^{33}$P)phosphine oxide agonist of the TRP-M8 is administered to human cancer patients, the level of TRP-M8 expression in the neoplastic tissues should be determined. A standard polymerase-chain reaction of the mRNA for the receptor may be used on biopsied tissues. Alternatively, ($^{32}$P or $^{33}$P)-phosphine oxide radioreceptor binding to the biopsied tissues may be measured. Also, the non-radioactive phosphine oxide agonist may be tested on the lips of the patient to determine the presence of the receptor, although the cutaneous effects of this receptor stimulation may not correlate to levels of TRP-M8 in neoplastic cells.

A second consideration before administering to human cancer patients is that of toxicity. To avoid irradiation of the TRP-M8 receptor in normal tissues, the drug can be delivered locally into the tumor or into the regional circulation of the malignant tissues. If the radioactive drug is to be administered by oral intake or by intravenous injection, it may be possible to protect the TRP-M8 in normal tissues from the radiation by topical administration of the non-radioactive drug. For example, the non-radioactive ligand may be administered as a lozenge, in chewing gum, or as a capsule or pill, to protect the mucous lining of the gastrointestinal tract against the radionuclide. Eye-drops and nose-drops containing the non-radioactive ligand may also be administered to protect the TRP-M8 receptors in these tissues.

The choice of the $^{32}$P or the $^{33}$P isotope for drug formulation would be determined by the circumstances of use, and the advantages of each isotope do not preclude use of the other. For example, if very high specific radioactivity is required $^{33}$P may be preferred to $^{32}$P because its lower energy emission may reduce potential radiolysis of the drug molecule. Also, $^{33}$P may be preferred to $^{32}$P because of its longer half-life and hence, a longer shelf-life for the drug. For example, a $^{32}$P compound will retain only 8.9% of its radioactivity 50 days after synthesis. By contrast, a $^{33}$P compound will retain 25.8% of its radioactivity. It is probable, however, that the $^{32}$P isotope would be the first choice for synthesis because radiologists are familiar with $^{32}$P properties in the clinic.

I also contemplate the possibility that sulfoxides and sulfones having the formula of $R_1$, $R_2$ and $R_3$—C $^{35}$SO$_x$R', where $R_1$, $R_2$ and $R_3$ are alkyl, together providing 6–18 carbon atoms, and preferably 5–10 carbons, and where $x$ is 1 (sulfoxide) or 2 (sulfones), and R' is alkyl may be used in practicing this invention. (see Rowsell et al. U.S. Pat. No. 4,070,449, issued Jan. 24, 1978, herein incorporated by reference). These compounds have cooling actions and hence affinity for the TRP-M8 receptor. The radioactive $^{35}$S-sulfoxides and sulfones would be easily prepared by oxidation of the corresponding sulfides.

In U.S. Pat. No. 4,020,153, issued April 26, herein incorporated by reference, Rowsell and Spring describe certain non-radioactive cyclic sulfinamides and sulfonamides having cooling effects. The general formula of these cyclic sulfinamides and sulfinamides is R—SO$_x$NR$_1$R$_2$ where R is a cycloalkyl, e.g. cyclohexyl, and $x$ is 1 (sulfinamide) or 2 (sulfonamide) and R$_1$, R$_2$ are alkylene groups, taken together, of up to 6 carbon atoms, which are joined to the nitrogen atom thereby to form a nitrogen heterocycle. These sulfinamides and sulfonamides were prepared by reduction of the acid (sulfinyl or sulfonyl) chloride with the appropriate alkylamines.

Acyclic sulfinamides and sulfonamides were also described by Rowsell and Hemms (U.S. Pat. No. 4,034,109, issued Jul. 5, 1977, herein incorporated by reference) having the general formula R—SO$_x$NR$_1$R$_2$, wherein R is a secondary or tertiary alkyl group of 5–12 carbon atoms, and R$_1$R$_2$, when taken separately, each represent hydrogen or a C$_1$–C$_{12}$ alkyl or hydroxyalkyl group, and together provide a total of no more than 12 carbon atoms and $x$ is 1 (sulfinamide) or 2 (sulfonamide). The $^{35}$S-forms of these sulfinamides and sulfonamides are contemplated for use in the practice of the present invention.

It is well understood in the art of cancer chemotherapy that a single agent may not be sufficient to control the growth and spread of disease. Thus, other agents may be used in combination with the present invention. Also, the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

EXPERIMENTAL

Example 1

Synthesis of WS148* (Exemplary Radioactive Phosphine Oxide)

A ($^{32}$ or $^{33}$P)-phosphine oxide radioligand of the invention, such as diisobutyl-n-heptylphosphine($^{32\ or\ 33}$P) phosphine oxide (coded as WS148*), is synthesized, for example, at 25 Ci/mmole. The non-radioactive form of this chemical is known to be potent and active on the TRP-M8 receptor.

The radiosynthesis of WS148* begins with the formation of the phosphorus-carbon bond starting from the most readily available precursors, [$^{32}$P]-phosphoric acid (H$_3$PO$_4$) or [$^{33}$P]-phosphoric acid. These starting materials are obtainable at high specific activity (up to 3000 to 6000 Ci/mmole) from Amersham Biosciences. For this example, the method of Zhang and Casida, supra, will be used, and the radioisotope selected is $^{33}$P.

An aqueous solution of [$^{33}$P]-H$_3$PO$_4$ is treated with phosphorus pentachloride (PCl$_5$), resulting in conversion not only of H$_2$O (the solvent) to POCl$_3$ but also of [$^{33}$P]-H$_3$PO$_4$ to [$^{33}$P]-POCl$_3$. Under reflux in toluene [$^{33}$P]-POCl$_3$ is reduced to [$^{33}$P]-PCl$_3$ with PPh$_3$ (triphenylphosphine), which is then hydrolyzed to [$^{33}$P]-H$_3$PO$_3$ (phosphorus acid). Using 1-bromo-n-heptane as the solvent, subsequent reaction of [$^{33}$P]-H$_3$PO$_3$ with BSTFA (N,O-bis(trimethylsilyl) trifluoroacetamide) yields the n-heptyl-[$^{33}$P]-P-(OTMS)$_3$ [tris(trimethylsilyl)phosphite] complex. Mild hydrolysis gives essentially the pure [$^{33}$P]-n-heptylphosphonic acid with 70% overall chemical and radiochemical yields. The incorporation efficiency of radioactivity is nearly quantitative.

The detailed methods are as follows. An aqueous solution of [$^{33}$P]-H$_3$—PO$_4$ (30 Ci in about 1 mg in 1.0 mL of water) in a 50-mL pear-shaped flask is mixed with K$_2$CO$_3$ (1.0 mg)

and taken to dryness by rotary evaporator at 30° C. Water (100 μL) was added into the flask. PCl$_5$ (1.0 g granules, 4.8 mmol) is placed in a dropping funnel connected to the flask through a condenser. The flask is immersed in a dry ice-acetone bath, freezing the water. The reaction is initiated by addition of a small portion of PCl$_5$, removing the cooling bath and allowing the ice to thaw and the mixture to react with PCl$_5$. This cycle is repeated until the reaction with PCl$_5$ is no longer violent before the addition of all the remaining PCl$_5$. [At this step, the [$^{33}$P]-POCl$_3$ is formed and may be used as an intermediate precursor for the synthesis of labeled phosphine oxides, using methods well known to the art]. The flask is then heated with an oil bath at 90° C. for 15 min, after which toluene (10 mL) is added and this temperature is maintained for another 15 min. The reaction is then cooled to room temperature, and PPh$_3$ (1.5 g, 5.7 mmol) is introduced. The solution is gently refluxed for 4.5 h and then distilled into a round-bottom flask (100 mL) cooled by a dry ice-acetone bath. Into the distillate is added a solution of water (0.25 g, 14 mmol) in THF (3.0 mL) at −78° C. The solution is stirred at this temperature for 15 min, and then the solvents are removed by vacuum, leaving [$^{33}$P]-H$_3$—PO$_3$ as a residue. 1-Bromo-n-heptane (12 mL) is added into the flask. The air is completely removed with vacuum, and argon was introduced. BSTFA (4.4 mL, 16 mmol) is then dropped in with a syringe. The resulting solution is refluxed for 2 h and then cooled. Residual reactants and some byproducts are removed by vacuum at room temperature. The remaining liquid is treated with a mixture of methanol (10 mL) and water (2 mL) and kept at room-temperature overnight. Methanol and water are removed by rotary evaporator. The residue (0.5 mL) was further azeotropically dried with absolute ethanol. The by-product trifluoromethylacetamide is completely removed at 60° C. by vacuum. The final product is essentially pure [$^{33}$P]-n-heptyl-phosphonic acid. The procedures are then repeated with PCl$_5$, but instead of PPh$_3$, the Grignard reagent, isobutylmagnesium bromide is added in excess (5 grams) and the mixture refluxed in toluene. The final product WS158* is a clear oily liquid with a mass spectra (+1 Dalton) and liquid chromatographic pattern identical to the non-radioactive product.

It should be noted that, in the above synthesis, alkyl or cycloalkyl substituents can be singly added onto [*P]-POCl$_3$ or [*P]-H$_3$—PO$_3$ using methods well known to the art. The use of PPh$_3$ and BSTFA is only one example of such technology for single addition of alkyl groups to the phosphine oxide, and alternative methods are available.

Example 2

Radioreceptor Assay

The synthesized radioligand of the invention, such as WS148* (diisobutyl-n-heptylphosphine($^{33}$P)oxide, for example, at a specific activity of 25 Ci/mmole is now used for a radioreceptor assay. In a standard test-tube method for competitive receptor binding, a tissue known to contain the TRP-M8 receptor, such as dorsal root ganglia neuronal cultures or a human prostate cancer cell line, is incubated with WS148* until steady-state conditions are reached (usually 30 to 60 minutes). The bound radioactive ligand is then separated from the free radioactive ligand by methods well known in the art such as filtration, centrifugation, dialysis, or size exclusion chromatography. To separate specific (receptor) binding from non-specific binding a non-radioactive phosphine oxide, such as iso-butyl-sec-butyl n-heptyl phosphine (a compound known as WS146, see Rowsell and Spring, supra) oxide, may be used to differentiate between total binding and non-specific binding. After these parameters are established, the next procedure is to conduct a saturation experiment that will establish the Kd and the Bmax (which is the density of receptors in a given tissue and is a pharmacological technique well known in the art). Various concentrations of radioactive ligand are incubated with the receptor preparation and the ratio of the bound and free levels of radioactive ligand is measured. The standard Rosenthal plot or Scatchard analysis of the binding data will yield the constants Kd and Bmax.

These and other uses of the present invention will become readily apparent to the skilled artisan once he or she has read the disclosure in this application.

It is to be understood that while the invention has been described above in conjunction with preferred specific embodiments, the description and examples are intended to illustrate and not limit the scope of the invention, which is defined by the scope of the appended claims.

It is claimed:

1. A radioactive $^{32}$P phosphine oxide composition, comprising R$_1$, R$_2$ and R$_3$ radicals linked to P=O wherein:

R$_1$ is an alkyl radical containing at least 3 carbon atoms,

R$_2$ is an alkyl radical containing at least 3 carbon atoms or a cycloalkyl radical and R$_3$ is an alkyl or cycloalkyl radical, R$_1$, R$_2$ and R$_3$ together present a total of from 13–17 carbon atoms, and At least one of R$_1$, R$_2$ and R$_3$ has branching in an α, β, or γ position relative to the $^{32}$P (phosphorus) atom.

2. A radioactive $^{33}$P phosphine oxide composition, comprising R$_1$, R$_2$ and R$_3$ radicals linked to P=O wherein:

R$_1$ is an alkyl radical containing at least 3 carbon atoms,

R$_2$ is an alkyl radical containing at least 3 carbon atoms or a cycloalkyl radical and R$_3$ is an alkyl or cycloalkyl radical, R$_1$, R$_2$ and R$_3$ together present a total of from 13–17 carbon atoms, and At least one of R$_1$, R$_2$ and R$_3$ has branching in an α, β, or γ position relative to the $^{33}$P (phosphorus) atom.

3. A composition comprising:

a radioactive trialkyl or dialkylcycloalkyl phospine oxide having the structure R$_1$ R$_2$, R$_3$ [* P]=O, wherein *P is $^{32}$P or $^{33}$P, and wherein the radioactive phosphine oxide has a high affinity for the TRP-M8 receptor and wherein R$_1$ is an alkyl radical containing at least 3 carbon atoms, R$_2$ is an alkyl radical containing at least 3 carbon atoms or a cycloalkyl radical, R$_3$ is an alkyl or cycloalkyl radical, and R$_1$, R$_2$ and R$_3$ together present a total of from 13–17 carbon atoms.

4. The composition as in claim 3 wherein the phosphine oxide has a specific activity of about 25 Ci/mmol or greater.

5. The radioactive compound diisobutyl-n-heptylphospine oxide wherein the phosphorus of the phosphine moiety is $^{32}$P or $^{33}$P.

6. The radioactive compound iso-butyl-sec-butyl n-heptyl phosphine oxide wherein the phosphorus of the phosphine moiety is $^{32}$P or $^{33}$P.

7. The composition as in claim 3 wherein the affinity of the radioactive phosphine oxide for the TRP-M8 receptor is sufficient for radioreceptor use.

* * * * *